US00PP15811P2

(12) United States Plant Patent
de Jong

(10) Patent No.: US PP15,811 P2
(45) Date of Patent: Jun. 28, 2005

(54) *AGAPANTHUS* PLANT NAMED 'WHITE HEAVEN'

(50) Latin Name: *Agapanthus africanus*
Varietal Denomination: White Heaven

(76) Inventor: Kees C J de Jong, Rnoordeinde 165 B, Reyerskoop 303 Boskoop (NL), 2771 BL ( * ) Notice: Subject to any disclaimer, the term of this patent is extended or adjusted under 35 U.S.C. 154(b) by 61 days.

(21) Appl. No.: 10/668,018

(22) Filed: Sep. 23, 2003

(51) Int. Cl.[7] ..... A01H 5/00
(52) U.S. Cl. ..... Plt./263

(58) Field of Search ..... Plt./263, 313

(56) References Cited

PUBLICATIONS

UPOV–ROM GTITM Computer Database 2009/05, GTI Jouve Retrieval Software, Citation for 'White Heaven'.*

* cited by examiner

*Primary Examiner*—Howard J. Locker

(57) ABSTRACT

A new cultivar of *Agapanthus* named 'White Heaven' that is characterized by an upright, clumping habit, green leaves and large many flowered flowerheads. In combination these traits set 'White Heaven' apart from all other existing varieties of *Agapanthus* known to the inventor.

2 Drawing Sheets

Genus: *Agapanthus.*
Species: *africanus.*
Denomination: White Heaven.

BACKGROUND OF THE INVENTION

The present invention relates to a new and distinct cultivar of lily-of-the-Nile grown for use as an ornamental for container, landscape or cut flowers. The new cultivar is known botanically as *Agapanthus africanus* and will hereinafter be referred to as 'White Heaven'.

'White Heaven' is a chance seedling that was discovered by the inventor in a cultivated area of Roelofarendsveen, The Netherlands in 1998. 'White Heaven' was discovered as an individual chance seedling in an established block of unknown cultivars of *Agapanthus africanus* being grown for the purpose of cut flower production. 'White Heaven' was selected, by the inventor, for the unique trait of large flower heads with 70–80 white flowers per inflorescence.

The new variety 'White Heaven' is a chance hybrid that resulted from the open pollination of unknown cultivars of *Agapanthus* grown from bulbs in a cultivated area of The Netherlands. The female parent is presumed to be an unknown cultivar of *Agapanthus africanus* and the male parent is presumed to be an unknown cultivar of *Agapanthus africanus.* The unique trait that distinguishes 'White Heaven' from the parent plants, is the size of the flower head, which is 150% larger than the closest comparison plant *Agapanthus africanus* 'Albus' (unpatented).

'White Heaven' is an herbaceous perennial, exhibiting an upright clumping growth habit, large white flower heads and green foliage. The size of the flower head, distinguishes 'White Heaven' from all other existing *Agapanthus* known to the inventor.

'White Heaven' was first asexually propagated in 1999 in a cultivated area of Roeloforendsveen, The Netherlands by the inventor. The method used for asexual propagation was division. Since that time under careful observation, successive generations have been determined stable and true to type. Asexual propagation can also be accomplished using the method of tissue culture.

The Inventor filed on May 28, 1999 Application Number 1999/0781 for a grant of European Community Plant Breeder's Rights. Application was granted on Mar. 5, 2001 (Grant Number 7,376). The Inventor has been engaged in the build-up of stock, by division, solely at Inventor's own nursery. No plants of 'White Heaven' have been sold or otherwise distributed from the Inventor's nursery prior to May 13, 2003.

SUMMARY OF THE INVENTION

The following traits have been repeatedly observed and represent the distinguishing characteristics of the new *Agapanthus* variety known as 'White Heaven'. These traits in combination distinguish 'White Heaven' from all other existing varieties of *Agapanthus* known to the inventor. 'White Heaven' has not been tested under all possible conditions and phenotypic differences may be observed with variations in environmental, climatic, and cultural conditions, however, without any variance in genotype.

1. *Agapanthus* 'White Heaven' is evergreen.
2. *Agapanthus* 'White Heaven' exhibits vertical scapes and large flower heads.
3. *Agapanthus* 'White Heaven' exhibits 70–80 white flowers per inflorescence.
4. *Agapanthus* 'White Heaven' exhibits an upright and clumping habit.
5. *Agapanthus* 'White Heaven' is an ornamental herbaceous perennial.
6. *Agapanthus* 'White Heaven' exhibits green foliage.
7. *Agapanthus* 'White Heaven' is suitable for cut flowers, and as a container or landscape plant.
8. *Agapanthus* 'White Heaven' is 90 cm. in height and 75 cm. in width at maturity.
9. *Agapanthus* 'White Heaven' is hardy to USDA Zone 8b.

BRIEF DESCRIPTION OF THE DRAWINGS

The accompanying color drawings illustrate the overall appearance of the new *Agapanthus* variety 'White Heaven' at three years old and grown in a container, showing the colors as true as it is reasonably possible to obtain in colored reproductions of this type.

The drawing on sheet 1 illustrates the entire plant in bloom from a side perspective.

The drawing on sheet 2 shows a close-up view of the flowers.

Colors in the drawings may differ from the color values cited in the detailed botanical description, which accurately describe the actual colors of the new variety 'White Heaven'. The drawings were made using conventional photographic techniques and although flower and foliage colors may appear different from actual colors due to light reflectance, they are as accurate as possible by conventional photography.

BOTANICAL DESCRIPTION OF THE PLANT

The following is a detailed description of the new *Agapanthus* cultivar named 'White Heaven'. Color determinations are in accordance with The 2001 Royal Horticultural Society Colour Chart except where general color terms of ordinary dictionary significance are used. The growing requirements are similar to the species.

Botanical classification: *Agapanthus* 'White Heaven'.
Commercial classification: Ornamental.
Species: *Africanus.*
Common name: Lily-of-the-Nile.
Use: Ornamental plant suitable for massing in landscape, container plant or cut flowers.
Type: Herbaceous perennial.
Parentage: The chance hybrid 'White Heaven' is presumed to have resulted from the open pollination of unknown cultivars of the following parent plants:
- *Presumed female parent plant.*—Unknown cultivar of *Agapanthus africanus* grown from bulb.
- *Presumed male parent plant.*—Unknown cultivar of *Agapanthus africanus* grown from bulb.

Growth rate: Slow growing, an average of 2 shoots per year.
Growth habit: Upright, clumping habit.
Branching habit: Leaves are arching and flower stems vertical.
Plant height (at maturity): 90 cm. in height.
Plant width (at maturity): 75 cm. in width.
Plant shape: Fountain-shaped, with arching leaves and vertical flower stalks.
Hardiness: USDA Zone 8b.
Propagation: Asexual propagation is accomplished using division or tissue culture.
Root system: Fleshy.
Pollination requirements: None observed.
Sexuality: Bisexual flowers.
Cultural requirements: Plant in full sun and well-drained sandy soil.
Cropping time: Approximately 12 months from division to a 1-liter container.
Seasonal interest: Spring, summer and fall flowers.
Diseases and pests: Protect from snails and slugs. No serious problems known to the inventor.
Special growing considerations: Avoid allowing plant to become dry.

Foliage:
- *Type.*—Evergreen.
- *Leaf shape.*—Narrow linear.
- *Leaf form.*—Arching.
- *Leaf arrangement.*—Leaves grow directly from rootstock.
- *Leaf apex.*—Acute.
- *Leaf base.*—Broad cuneate.
- *Leaf division.*—Simple.
- *Leaf attachment.*—Mostly sessile but some slightly sheathing.
- *Leaf margins.*—Entire.
- *Leaf color* (*adaxial surface*).—Closest to 137A.
- *Leaf color* (*abaxial surface*).—Closest to 137B.
- *Leaf surface* (*adaxial surface*).—Glabrous.
- *Leaf surface* (*abaxial surface*).—Glabrous.
- *Pubescence.*—None.
- *Venation pattern.*—Parallel.
- *Color of veins* (*abaxial and adaxial surfaces*).—137B.
- *Leaf length.*—65 cm. in length.
- *Leaf width.*—4 cm. in width.
- *Leaf fragrance.*—None observed.
- *Stipules.*—None observed.

Flower:
- *Flowering months.*—From early June to late July.
- *Inflorescence type.*—Umbel.
- *Number of flowers per umbel.*—75–80 flowers per umbel.
- *Persistent or self-cleaning.*—Self-cleaning.
- *Flower type.*—Solitary.
- *Flower aspect.*—Facing upward and outward.
- *Pedicel color.*—Green, 143B.
- *Pedicel dimensions.*—8.3 cm in length; 2 mm in width.
- *Pedicel shape.*—Circular.
- *Pedicel surface.*—Smooth, slightly glossy.
- *Flower bud description at approximately five days prior to opening.*—Shape: Narrow, obovate. Dimensions: 2.6 cm in length; 1 cm average width. Color: White, 155C; at base, green-white, 157D. Surface: Smooth, slightly glossy.
- *Flower dimensions.*—4.5 cm. in length and 4.5 cm. in width.
- *Depth of corolla tube.*—1.4 cm. in depth.
- *Dimensions of scape.*—Average of 65 cm. in length and 16 mm. in width.
- *Scape color.*—137A.
- *Scape texture.*—Pithy.
- *Shape of scape.*—Cylindrical.
- *Scape surface.*—Mostly glabrous but with areas of slight down.
- *Flower shape.*—Campanulate.
- *Petals.*—Apetalous.
- *Number of tepals.*—Ranges from 6–9 in number, with an average of 7.
- *Tepals fused or unfused.*—Basally fused.
- *Tepal shape.*—Narrow obovate.
- *Tepal margin.*—Entire.
- *Tepal surface* (*adaxial surface*).—Glabrous.
- *Tepal surface* (*abaxial surface*).—Glabrous.
- *Tepal color* (*adaxial and abaxial surfaces*).—155D.
- *Tepal dimensions.*—3.50 cm. in length and 1 cm. in width.
- *Flower fragrance.*—None.

Reproductive organs:
- *Stamens.*—6 in number.
- *Stamen color.*—155B.
- *Stamen dimensions.*—3 cm. in length.

*Stigma color.*—155C.
*Anther dimensions.*—Dorsifixed, kidney-shaped, average length: 2 mm.
*Anther color.*—Grey-orange, 163B.
*Pistil dimensions.*—One present, 2.8 cm in length, of which length of pistil style 2.75 cm.
*Pistil color.*—White.
*Filament dimensions.*—Length (average) 3.7 cm.
*Filament color.*—White 155C.
*Pollen quantity.*—Much, color: yellow, 12A.
*Ovary shape.*—Obovate to elliptic.
*Ovary position.*—Inferior.
*Ovary dimensions.*—Length (average) 1.3 cm; width (average) 5 mm.
*Ovary color.*—Yellow-green, 150C.

Seed production:
*Number of seeds.*—Average of four per capsule.
*Seed shape.*—Flat and oval.
*Fruit.*—Capsule.
*Fruit color.*—Off-white.
*Fruit size.*—Moderately large.
*Fruit shape.*—Flattened and oblong.
*Fruit surface.*—Glossy.
*Seed size.*—Moderately large.
*Seed color.*—Dark brown to black.
*Seed surface.*—Waxy.

It is claimed:

1. A new and distinct variety of *Agapanthus* plant named 'White Heaven' as described and illustrated.

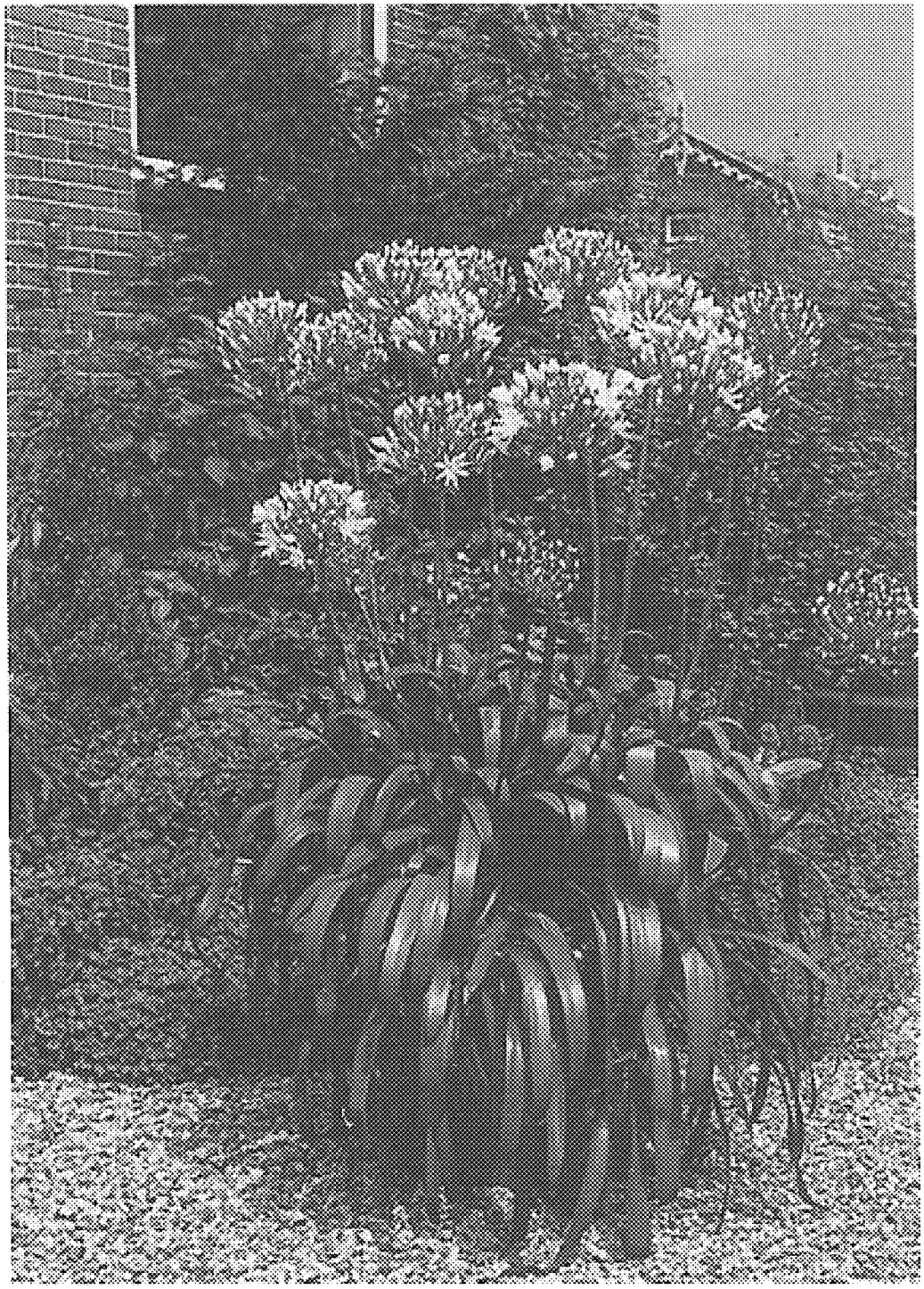

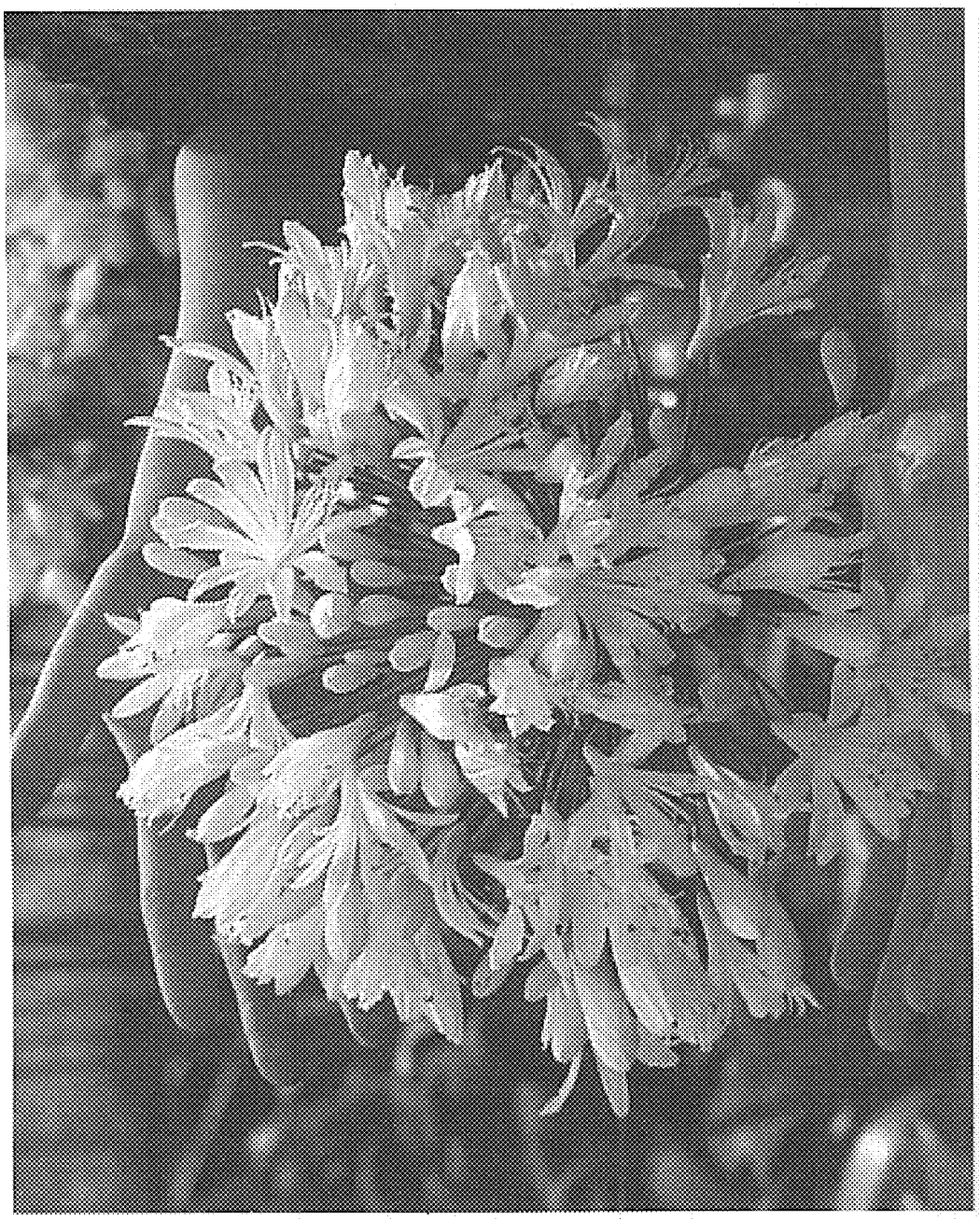

* * * * *